United States Patent [19]

Minchinton

[11] Patent Number: 5,602,028
[45] Date of Patent: Feb. 11, 1997

[54] SYSTEM FOR GROWING MULTI-LAYERED CELL CULTURES

[75] Inventor: Andrew I. Minchinton, Vancouver, Canada

[73] Assignee: The University of British Columbia, Vancouver, Canada

[21] Appl. No.: 497,587

[22] Filed: Jun. 30, 1995

[51] Int. Cl.$^6$ ................................ C12N 5/00; C12M 3/00
[52] U.S. Cl. ................... 435/401; 435/297.1; 435/297.2; 435/297.5; 435/399; 210/615
[58] Field of Search ............................ 435/297.1, 297.2, 435/297.5, 240.241; 210/615, 644

[56] References Cited

U.S. PATENT DOCUMENTS

| | | | |
|---|---|---|---|
| 4,667,504 | 5/1987 | Hobson | 73/38 |
| 4,812,407 | 3/1989 | Buchmann et al. | 435/297.1 |
| 5,139,951 | 8/1992 | Butz et al. | 435/297.5 |
| 5,160,440 | 11/1992 | Naughton et al. | 435/284 |
| 5,183,760 | 2/1993 | Sweetana et al. | 435/297.5 |
| 5,198,109 | 3/1993 | Hanson | 210/321.75 |

OTHER PUBLICATIONS

"Three–Dimensional Histoculture: Origins and Applications in Cancer Research" by Hoffman Cancer Cells 1991 vol. 3 No. 3.
"Multicellular Membranes: An In Vitro Model for Assessing Transport in the Extravascular Compartment of a Tumor"–Wilson et al.
15th Annual Meeting North American Hyperthermia Society Apr. 1–6 1995.
Multilayers of Cells Growing on a Permeable Support: An *In Vitro* Tumour Model. Studies with Radiation and Tirapazamine by Andrew I. Minchinton et al. Abstract 15 Jul. 1994–(inventor disclosure).

*Primary Examiner*—David A. Redding
*Attorney, Agent, or Firm*—C. A. Rowley

[57] ABSTRACT

Method and apparatus for growing cell cultures consisting of a plurality of layers includes a chamber for submerging cells in a medium while supporting and binding them to a semi-permeable membrane. A stirrer is positioned within the chamber and continuously stirs the medium to constantly circulate it past the exposed surface of a semi-permeable membrane on one side of the cell culture and along the exposed surface of the cell culture growing on the membrane and remote from the membrane to transfer nutrients to both surfaces of the cell either directly or through the membrane without disrupting the cell culture on the membrane. Preferably, multi-layered cell cultures so grown while still adhered to the membrane and growing is then mounted in a partition separating a pair of chambers to provide substantially the sole passage from one chamber to the other by flow through the multi-layer culture while in the living state whereby the rate of penetration or degree of penetration of a culture being tested by the material being tested may be measured by measuring the quantity of material in one chamber versus the quantity of that material in the other chamber.

20 Claims, 2 Drawing Sheets

SYSTEM FOR GROWING MULTI-LAYERED CELL CULTURES

FIELD OF THE INVENTION

The present invention relates to a method of growing multi-layered culture of cells and to a technique for measuring rate of penetration through the culture of cells by an agent (e.g. drug or pharmaceutical).

BACKGROUND OF THE INVENTION

The most commonly used method for assessing the penetration of agents (e.g. drugs and pharmaceuticals) into living tissue is the multi-cellular spheroid. Multicellular spheroids are a conglomeration of up to $10^6$ animal cells which form small balls of tissue and are grown in a flask in which the media is stirred (spinner culture). Penetration of agents into such multi-cellular spheroids can be monitored by applying the agent for a period of time, then removing spheroids, sectioning and then microscopically examining them.

The use of the spheroid system the measuring penetration is effective, but has several significant limitations. The geometry of the diffusion or transport into spheroids is almost inverse of some situations encountered in nature, i.e. in many instances drugs diffuse radially outward from capillaries within tissue, while with the spheroids the agent diffuses from the outer or maximum surface area toward the center of the sphere. The main drawback of using spheroids to measure penetration of an agent is the requirement that the concentrations of the agent at different depths of penetration cannot be determined easily. Usually after a period of time has lapsed to allow penetration of the test agent the spheroids are removed from the incubating medium and quickly frozen, so they may then be section and evaluated. When the agent is fluorescent it is microscopically evaluated. If radio labeled (which is expensive and more difficult) a photographic emulsion is applied and then the section microscopically evaluated. The agent must bind to the cells to permit dissociation from the spheroid and analysis using flow cytometry. If the agents are not readily identifiable (i.e. colored, fluorescent or radio labeled) spheroids cannot be used.

In some other conventional techniques for producing cells, the cells are grown as a single cell layer on a plastic or glass surface e.g. in a petri dish and have one face directly facing the petri dish so that substantially all the growth occurs from the opposite face. Cells stop growing when they reach confluence or form a super-confluence and become senescent due to oxygen/nutrient deprivation.

U.S. Pat. No. 5,160,490 issued Nov. 3, 1991 to Naughton et al. describes a three-dimensional cell culture system for culturing a variety of different cells and tissues in-vitro for extended periods of time by growing same on a pre-established stroma cell matrix.

In an article entitled "Three-Dimensional Histoculturez Origins and Applications in Cancer Research" by Hoffman published in *Cancer Cells*, March 1991, Volume 3 Number 3 a review of known techniques for growing three dimensional histocultures is presented and describes sponge-matrix cultures, Collagen-gel cultures, filter or mesh supported organ cultures and spheroids. The paper also reviews some studies of tumor cell migrations and invasion and drag sensitivity assays. None of these techniques is available for growing cell cultures in-vitro wherein the cell culture grown is at least 5 cells in thickness and wherein the so formed culture provides a relatively uniform thickness mat of cells which may then be used to investigate the effectiveness of applied reagents.

Currently, anti-cancer agents are mainly evaluated experimentally using in-vitro methods (cells growing in mono layers or in suspension cultures or spheroids) and in-vivo systems utilizing animals, i.e. to determine their activity in-vitro against cells in the mono layer culture. When an active agent is identified, the compound is transferred to in-vivo testing systems wherein it is administered to animals and the effect against tumors such as implated tumors is assessed. This transfer from in-vitro to in-vivo testing is generally quite problematic in that the animal physiology and the process of drug absorption, distribution, and the metabolism of the animal and various excretions often alter the behavior of the drugs from that predicted by the in-vitro studies.

U.S. Pat. No. 4,667,504 issued May 26, 1987 to Hobson; 5,183,760 issued Feb. 2, 1993 to Sweetana et al. and 5,198,109 issued Mar. 30, 1993 to Hanson et al. each disclose diffusion cells as means for testing the diffusion of chemicals through a membrane of cells. Similar systems to those disclosed in the patents are sold by Corning Costar corporation under the trademark COSTAR.

One of the major problems that is encountered in administering drugs to counteract a tumor growth, is the requirement of the drug to penetrate the tumor and there are few means available to assess such penetration.

BRIEF DESCRIPTION OF THE PRESENT INVENTION

It is an object of the present invention to provide a method and apparatus for growing multi-layer cell cultures.

It is a further object of the present invention to provide a system for assessing pharmaceuticals for their activity and their ability to penetrate tissue.

Broadly, the present invention relates to an apparatus for growing multi-layered cell culture mats comprising a growth chamber, a support means a permeable membrane having a cell culture adhered to one of its major surfaces, said support means supporting said membrane and said cell culture submerged in a liquid growth medium so that the liquid growth medium contacts both major surfaces of the membrane, stirring means in the chamber to vigorously stir the liquid medium and move said medium to flow over both major surfaces of the membrane at a speed to adequately deliver nutrients to the cell culture adhered to and growing on one major surface of the membrane. The medium contacts the cell culture both directly via an exposed surface of cell culture remote from the one major surface of said membrane and through the permeable membrane and filter means are provided to permit the ingress of gases into the growth chamber to replace gases consumed in growing the cell culture while preventing the ingress of contaminating materials.

Preferably, the support means supports the membrane with its major surfaces substantially horizontal.

Preferably the membrane defines passages through the support means.

Preferably the stirring means will be positioned on the side of the support means being the major surface of said membrane opposite one major surface.

Preferably, the stirring will comprise a magnetic stir positioned within the chamber and driven by magnetic means outside of said chamber.

Preferably, the planer membrane will be mounted on and form a bottom wall in, an annular supporting ring and the support means will include means for releasably supporting the ring.

The present invention also relates to a method of growing a multi-layered cell culture comprising supporting and adhering a first major surface of culture formed by an initial seed layer of cells of the culture on a one major surface of a permeable membrane having two major surfaces, submerging the culture supported and adhered to one of the major surfaces of the membrane in a liquid cell growth medium for cells in the culture contained within a growth chamber, circulating the medium past the culture to deliver nutrients to the culture by passage through the membrane to the first major surface of the culture and directly to an exposed major surface of the cell culture remote from the membrane thereby to transfer nutrients from the medium to both major surfaces of the culture and grow a said cell culture into a multi-layered substantially planer cell culture mat on said membrane.

Preferably, gases will be supplied to the growth chamber containing the medium.

Preferably, growth of cells is continued by supply of nutrients to both said major surfaces of the mat to form a necrosis layer within the culture.

Preferably, the membrane is releasably held in the growth chamber by a supporting ring structure and the membrane and cell culture mat are transferred to a partition wall between a pair of side by side chambers each containing a liquid medium, the membrane and the mat providing the sole means of communication for liquid medium between the pair of chambers so that flow between the pair of chambers passes through the membrane and the mat.

Preferably, the liquid medium in both chambers of the pair of chamber will be the same.

Preferably, the method will further comprise inoculating a material to be tested into said liquid medium in one of the pair of chambers and measuring the amount of the material passing into the other chamber over a period of time.

Preferably, the liquid medium in each of the pair of chambers will be the same as the liquid cell growth medium.

Preferably, the liquid medium in each of the pair of chambers will be individually stirred.

Preferably, gases will be supplied into the pair of chambers.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

The multi-layered cell cultures grown using the present invention may be applied to a variety of different uses, but are particularly suited to investigating the effectiveness of drugs including anticancer agents in tissue like environments including tumors.

Figure 1:
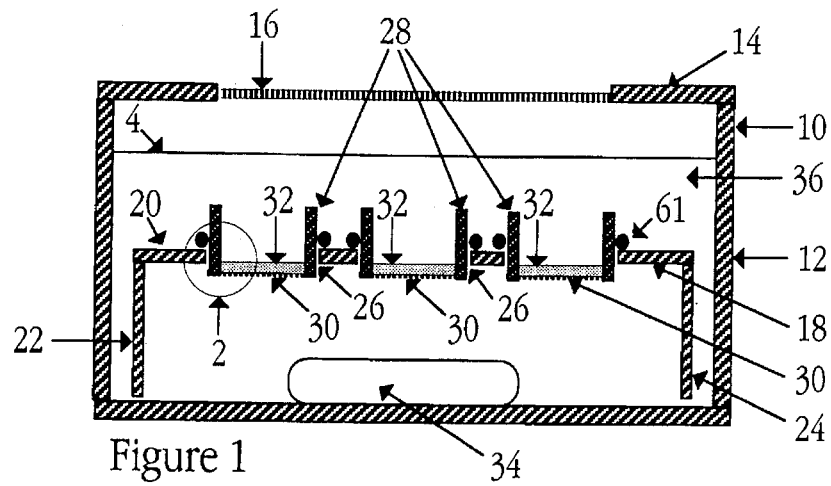
FIG. 1 is a section view through a primary growth chamber of the culture growing system of the present invention.

As shown in FIG. 1, the apparatus 10 for growing the multi-layered cell cultures of the present invention is composed of a growth container 12 having a lid 14 that hermetically seals with the container 12 to form a growth chamber and is provided with a hydrophobic gas filter 16 that permits the gas exchange including the ingress of sterile gases such as oxygen into the chamber 12 without contaminating the contents of the chamber.

A suitable supporting bridge structure 18 is removably positioned within the chamber 12. In the illustrated arrangement, the support structure 18 is formed with a main or top panel 20 and supported on legs 22 and 24 positioned one at each corner of the top panel 20. The panel 20 is proportioned relative to the circumference of the growth chamber 12 to provide adequate clearance between the periphery of the panel 20 and the adjacent walls of the chamber 12 to permit the circulation of growth medium around the panel 20.

Figure 2:
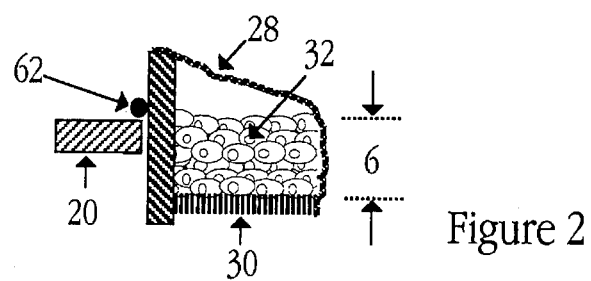
FIG. 2 is an enlarged view within the circle 3 of FIG. 1.

A plurality of membrane cup receiving hole 26 are formed into the top 20 of the bridge member 18 and a membrane cup 28 is positioned in each of these membrane receiving holes 26. Each membrane cup 28 is a substantially annular member or wall and has a transverse or bottom wall formed by a porous membrane 30 on which the cell culture mat 32 grows as will be described in more detail hereinbelow and as shown in more detail in FIG. 2.

Positioned on the bottom of the container 12 is a stirrer, preferably a magnetic type stir bar 34 which agitates the liquid growth medium 36 with which the chamber 12 is filled to a level L above the tops of the cups 28, preferably at least about 2.5 cm above the tops of the cups 28.

It will be noted that cups provide passages through the top 20 so that the major surface of the membrane 30 and thereby one major surface of the cell culture mat and the exposed other major surface of cell culture mat 32 are both in direct contact with the growth medium within the chamber 12.

Figure 3:
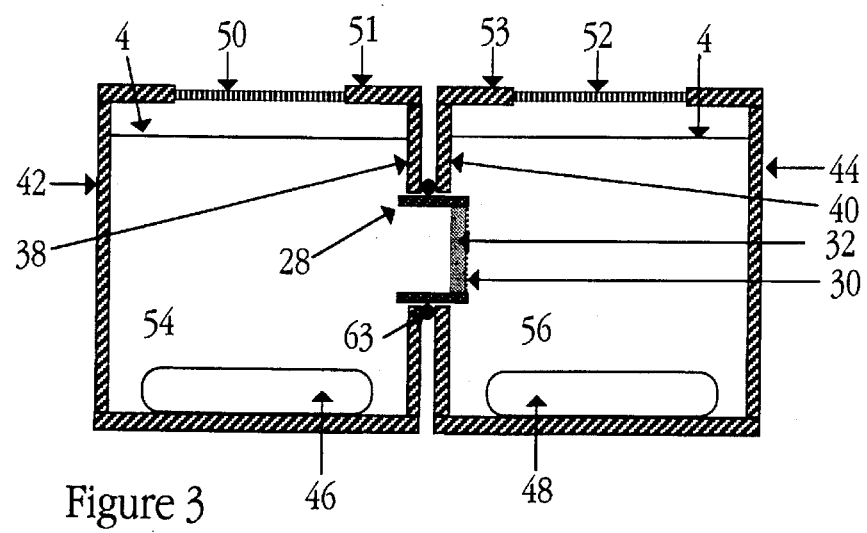
FIG. 3 is a cross-sectional view of a pair of chambers indicating the testing system of the present invention.

After the multi-layer mat 32 has grown to contain the desired number of cells, i.e. thickness T will be equal to a plurality of cells preferably at least 5 cells and generally closer to 20 cells, the membrane cup 28 together with membrane 30 and the cell culture mat 32 may be transferred to the apparatus shown in FIG. 3 with the cup 28 mounted so that it extends through the walls 38 and 40 of a pair of adjacent chambers 42 and 44. The cup 28 is sealed with the walls 38 and 40 so that the only passage between the chambers 42 and 44 is through the mat 32 and membrane 30. Each of the chambers 42 and 44 is provided with its own stirrer, preferable magnetic bar stirrer 46 and 48 respectively and each is also provided with a hydrophobic filter 50 and 52 respectively which is essentially the same as the hydrophobic filter 16. Each of the chambers 42 and 44 are filled to precisely the same level $L_1$ with liquid medium 54 and 56 which normally will be the same medium and preferably will be the same medium as the growth medium 36 used for drawing the cell culture mat 32 in the chamber 12.

To operate the present invention, the required number of membrane cups 28 each with a suitable permeable membrane 30 extending across its bottom end are positioned within the holes 26 in the upper wall 20. The suitable membranes 30 is marketed under the trade name Millicell-CM by Millipore™, since this material is both transparent to permit monitoring the growth of the cell and permits nutrients 36 to easily pass therethrough and feed the cells.

The membrane is provided with a tissue culture treated surface, for example by treating with collagen type 1 or other basement membrane proteins prior to seeding the cells to be grown.

It is important if multi-layered cell cultures are to be produced to ensure the required oxygen and nutrients are available to the cells so that they may grow. This requires vigorously stirring the media 36 within the growth chamber 12 so that the media contacts both faces of the cell culture 32 and delivers the nutrients as required. The oxygen inlet provided by the filter 16 ensures replenishment of the oxygen assuming the chamber is placed in the required environment.

EXAMPLE

In carrying out experiments with this system, each of the chambers 12 was fitted with a support structure 18 that contain 6 millicells, i.e. membrane cups 28 that were suspended in about 120 ml of growth media. The media was vigorously stirred during the growing period. The whole assembly was placed in a humidified 37° C. incubator gassed with 5% oxygen ($O_2$), 5% carbon dioxide ($CO_2$) and 90% nitrogen ($N_2$). The chamber 12 was sealed and a magnetic stirrer device was used as the stirrer so that the only inlet into the chamber 12 after the top 14 has been applied and sealed is through the hydrophobic filter membrane 16. This better ensures sterility.

Figure 4:
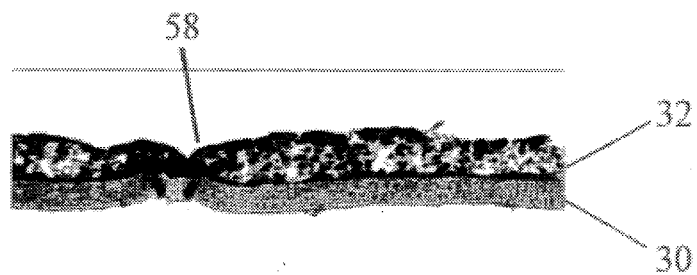
FIG. 4 shows multi-layered cell culture of SiHa cells grown for four days to a magnification of about 250 times.
Figure 5:
FIG. 5 is a view similar to FIG. 4 but showing the layered growth after eight days.
Figure 6:
FIG. 6 is a view similar to FIG. 4 but showing growth after 14 days in the development of the central necrosis.

The cells are grown to produce the cell culture mat 32 of the desired thickness of the multi-layered culture or mat by continuing the stirring and replacement of oxygen (and other gasses) through the filter 16. It will be apparent that the mat is substantially flat and that it has a relatively uniformly thickness above the membrane 30. FIG. 4 shows a SiHa cell culture mat formed after four days of growth. The mat after 4 days growth was relatively thin and had certain irregularities such as those shown at 58. However, after eight days, growth the mat 32 became reasonably uniform and was about 15 cells (see FIG. 5) thick. FIG. 6 shows a cell culture wherein the growth has extended so far from both major surfaces that the cells in the middle are starved and form a central necrosis. This is similar to the growth of solid tumors seen in vivo.

When the mat 32 has grown to the desired thickness for testing the cups 28 containing the cell culture mat 32 are transferred to the apparatus shown in FIG. 3 and define the sole passage between the chambers 42 and 44. The chambers 42 and 44 are each filled to the same levels L1 so that there are substantially no hydrostatic forces acting through the membrane 30 and mat 32 and the mediums 54 and 56 in these two chambers 42 and 44 are stirred.

By using as the medium 54 and 56, the same growth medium as used in the chamber 12, i.e. the medium 36, the growth of the cells may be continued within the cup 28 between the chambers 42 and 44, The oxygen (and other gases) used is replaced into chambers 42 and 44 through the filters 50 and 52 provided in the tops 51 and 53 of the chambers 42 and 44. The chambers 42 and 44 function essentially the same manner as the chamber 12 when operating as growth chambers. It has been found that the use of 50 ml of medium in each of the chambers 42 and 44 was adequate provided, of course, the cell cultures are fully submerged. This device is placed in an incubator replicating the conditions in which the cell culture mat 32 was grown.

The cell culture mats so treated have been found to be viable and intact for up to five days after the transfer.

To assess the effectiveness of drugs or the like to pass through the culture mats, the compound to be tested is added to one of the chambers, say chamber 42, and aliquots of the media are removed at intervals and the concentration of the compound and any metabolites is measured.

In a specific example, an 8 day old multi-layered cell culture of SiHa cells was exposed on one side to a media containing 125 or 150 μ moles per liter of a radiosensitizer and the series of aliquots were removed from both reservoirs at different times. Within 40 hours, the untreated reservoir reached concentrations of 8% of the drug treated reservoir in the case of misonidazole, and 9% in the case of etanidazole. The results are consistent qualitatively on the basis of the partition coefficients of these compounds and is a clear indication of the feasibility of the present method.

It would be convenient to have a system whereby the thickness of the mat could be accommodated in the test method without requiring measurement. The thickness of the cell culture cannot be precisely controlled and therefore will vary slightly and these variations will likely influence the speed of penetration of the pharmaceutical through the multi celled culture. One such system includes simultaneously placing both a known marker compound with known penetration characteristics and a pharmaceutical having unknown penetration characteristics in a known ratio into one of the chambers and then monitoring the ratio of these two drugs either in the other chamber or the change in the ratio in the inoculated chamber will permit determining the rate of penetration of the pharmaceutical with unknown characteristics based on the ratio and the known rate of the penetration of the known drug i.e. the speed of penetration of the unknown is measured relative to the marker compound provide.

The rate of drug depletion or disappearance from the inoculated chamber is directly proportional to the ability of the drug to penetrate tissue. The rate of appearance of the unchanged drug in the other chamber (receiving chamber) is a product of penetration and metabolism and the difference between the rates of disappearance from the inoculation chamber and appearance in the receiving chamber is a result of the metabolism of the drug.

Having described the invention, modifications will be evident to those skilled in the art without departing from the scope of the invention as defined in the appended claims.

I claim:

1. An apparatus for growing multi-layered cell culture mats comprising a growth chamber, a support means, a permeable membrane having two major surfaces with a cell culture adhered to a one of said major surfaces, said support means supporting said membrane in said chamber in a position wherein said membrane is submerged in a liquid growth medium when said chamber is filled to a selected degree so that said liquid growth medium contacts both surfaces of said membrane, stirring means in said chamber, said stirring means being sized to vigorously stir said liquid medium and move said medium to flow over both said major surfaces of said membrane at a speed to adequately deliver nutrients to said cell culture adhered to and growing on said one major surface of said membrane, said medium contacting said cell culture both directly via an exposed surface of cell culture remote from said one major surface of said membrane and through said permeable membrane and filter means to permit the ingress of gases into said growth chamber to replace gases consumed in said growing of said cell culture while preventing the ingress of contaminating materials into said growth chamber.

2. An apparatus as defined in claim 1 wherein said support means supports said membrane with its major surfaces substantially horizontal.

3. An apparatus as defined in claim 1 wherein said stirring means is positioned on the side of said support means facing the other of said major surfaces of said membrane.

4. An apparatus as defined in claim 3 wherein said stirrer comprises a magnetic stir bar positioned within said chamber and driven by magnetic means outside of said chamber.

5. An apparatus as defined in claim 1 wherein said membrane is mounted on and forms a bottom wall in an annular supporting ring and said support means includes means for releasably supporting said ring.

6. An apparatus as defined in claim 2 wherein said membrane is mounted on and forms a bottom wall in, an annular supporting ring and said support means includes means for releasably supporting said ring.

7. An apparatus as defined in claim 3 wherein said membrane is mounted on and forms a bottom wall in, an annular supporting ring and said support means includes means for releasably supporting said ring.

8. A method of growing a multi-layered cell culture comprising supporting and adhering a first major surface of an initial seed layer of cells of said culture on one major surface of a permeable membrane having a pair of opposed major surfaces, submerging said culture supported and adhered to said membrane in a liquid cell growth medium for cells in said culture contained in a growth chamber, circulating said medium past said culture to deliver nutrients to said culture by passage through said membrane to said one major surface of said cell culture and directly to an exposed second major surface of said cell culture remote from said membrane thereby to transfer nutrients from said medium to both said major surfaces of said cell culture and grow a said cell culture into a multi-layered substantially planer cell culture mat on said membrane.

9. A method as defined in claim 8 wherein gasses are supplied to said growth chamber containing said growth medium while preventing the ingress of contaminating materials.

10. A method as defined in claim 9 wherein said method is continued to grow cells and to form a necrosis layer within said cell culture mat.

11. A method as defined in claim 8 wherein said membrane is releasibly held in said growth chamber in a supporting ring structure and said method further comprising transferring said membrane and said cell culture mat to a partition wall between a pair of side by side chambers each containing a liquid medium, said membrane and said cell culture mat providing the sole means of communication for liquid medium between said a pair of chambers so that flow between said pair of chambers passes through said membrane and said cell culture mat.

12. A method as defined in claim 9 wherein said membrane is releasibly held in said growth chamber in a supporting ring structure and said method further comprising transferring said membrane and said cell culture mat to a partition wall between a pair of side by side chambers each containing a liquid medium, said membrane and said cell culture mat providing the sole means of communication for liquid medium between said a pair of chambers so that flow between said pair of chambers passes through said membrane and said cell culture mat.

13. A method as defined in claim 10 wherein said membrane is releasable held in said growth chamber in a supporting ring structure and said membrane and said cell culture mat said method further comprising transferring said membrane and said cell culture mat to a partition wall between a pair of side by side chambers each containing a liquid medium, said membrane and said cell culture mat providing the sole means of communication for liquid medium between said a pair of chambers so that flow between said pair of chambers passes through said membrane and said cell culture mat.

14. A method as defined in claim 11 wherein said liquid medium in both chambers of said pair chambers is essentially the same composition.

15. A method as defined in claim 11 wherein said method further comprises inoculating a material to be tested into said liquid medium in one of said pair of chambers and measuring the amount of said material passing into the other of said pair of chambers over a period of time.

16. A method as defined in claim 11 wherein said liquid medium in each of said pair of chambers is essentially the same composition as said liquid cell growth medium.

17. A method as defined in claim 8 wherein said liquid medium in each of said pair of chambers is individually stirred.

18. A method as defined in claim 12 wherein said method further comprises inoculating a material to be tested into said liquid medium in one of said pair of chambers and measuring the amount of said material passing into the other of said pair of chambers over a period of time.

19. A method as defined in claim 13 wherein said method further comprises inoculating a material to be tested into said liquid medium in one of said pair of chambers and measuring the amount of said material passing into the other of said pair of chambers over a period of time.

20. A method as defined in claim 16 wherein said method further comprises inoculating a material to be tested into said liquid medium in one of said pair of chambers and measuring the amount of said material passing into the other of said pair of chambers over a period of time.

\* \* \* \* \*